US00PP28133P3

(12) United States Plant Patent
van de Pol

(10) Patent No.: US PP28,133 P3
(45) Date of Patent: Jun. 20, 2017

(54) ***CAMPANULA* PLANT NAMED 'PTW1300101'**

(50) Latin Name: *Campanula portenschlagiana*
Varietal Denomination: PTW1300101

(71) Applicant: Peter van de Pol, Twello (NL)

(72) Inventor: Peter van de Pol, Twello (NL)

(73) Assignee: Genius Genes Production Facilities B.V., Twello (NL)

( * ) Notice: Subject to any disclaimer, the term of this patent is extended or adjusted under 35 U.S.C. 154(b) by 63 days.

(21) Appl. No.: 14/756,433

(22) Filed: Sep. 4, 2015

(65) Prior Publication Data

US 2017/0071119 P1 Mar. 9, 2017

(51) Int. Cl.
*A01H 5/02* (2006.01)

(52) U.S. Cl.
USPC ..... Plt./414

(58) Field of Classification Search
USPC ..... Plt./414
See application file for complete search history.

*Primary Examiner* — Keith Robinson
(74) *Attorney, Agent, or Firm* — C. A. Whealy

(57) ABSTRACT

A new and distinct *Campanula* plant named 'PTW1300101', characterized by its compact, upright to spreading and uniformly mounding plant habit; freely flowering habit; white-colored flowers; and good garden performance.

2 Drawing Sheets

Botanical designation: *Campanula portenschlagiana.*
Cultivar denomination: 'PTW1300101'.

BACKGROUND OF THE INVENTION

The present invention relates to a new and distinct *Campanula* plant, botanically known as *Campanula portenschlagiana* and hereinafter referred to by the cultivar name 'PTW1300101'.

The new *Campanula* plant is a product of a planned breeding program conducted by the Inventor in Twello, The Netherlands. The objective of the breeding program is to create new compact and freely-flowering *Campanula* plants that have good container and garden performance.

The new *Campanula* plant originated from a cross-pollination in July, 2011 of a proprietary selection of *Campanula portenschlagiana* identified as code number PTW-1200102S, not patented, as the female, or seed, parent with a proprietary selection of *Campanula portenschlagiana* identified as code number PTW-1100601S, not patented, as the male, or pollen, parent. The new *Campanula* plant was discovered and selected by the Inventor as a single flowering plant from within the progeny of the stated cross-pollination grown in a controlled greenhouse environment in Twello, The Netherlands in July, 2012

Asexual reproduction of the new *Campanula* plant by terminal vegetative cuttings in a controlled greenhouse environment in Twello, The Netherlands, since January, 2013, has shown that the unique features of the new *Campanula* plant are stable and reproduced true to type in successive generations.

SUMMARY OF THE INVENTION

Plants of the new *Campanula* plant have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'PTW1300101'. These characteristics in combination distinguish 'PTW1300101' as a new and distinct *Campanula* plant:

1. Compact, upright to spreading and uniformly mounding plant habit.
2. Freely flowering habit.
3. White-colored flowers.
4. Good garden performance.

Plants of the new *Campanula* differ from plants of the female parent selection primarily in the following characteristics:

1. Plants of the new *Campanula* have larger flowers than plants of the female parent selection.
2. Flowers of plants of the new *Campanula* are white in color whereas flowers of plants of the female parent selection have white-colored flowers with blue shading.

Plants of the new *Campanula* differ from plants of the male parent selection primarily in the following characteristics:

1. Plants of the new *Campanula* are more compact and uniform than plants of the male parent selection.
2. Leaves of plants of the new *Campanula* are darker green in color than leaves of plants of the male parent selection have white-colored flowers with blue shading.

Plants of the new *Campanula* can be compared to plants of *Campanula portenschlagiana* 'Get Mee White', not patented. In side-by-side comparisons conducted by the Inventor in Twello, The Netherlands, plants of the new *Campanula* differed primarily from plants of 'Get Mee White' in the following characteristics:

1. Plants of the new *Campanula* were more upright than and not as spreading as plants of 'Get Mee White'.

2. Leaves of plants of the new *Campanula* were darker green in color than leaves of plants of 'Get Mee White'.

BRIEF DESCRIPTION OF THE PHOTOGRAPHS

The accompanying colored photographs illustrate the overall appearance of the new *Campanula* plant showing the colors as true as it is reasonably possible to obtain in colored reproductions of this type. Colors in the photographs may differ slightly from the color values cited in the detailed botanical description which accurately describe the actual colors of the new *Campanula* plant.

The photograph on the first sheet is a side perspective view of a typical flowering plant of 'PTW1300101' grown in a container.

The photograph on the second sheet is a close-up view of a typical flowering plant of 'PTW1300101'.

DETAILED BOTANICAL DESCRIPTION

Plants used for the aforementioned photographs and following description were grown in 10.5-cm containers during the spring in a glass-covered greenhouse in Poeldijk, The Netherlands and under cultural practices typical of commercial *Campanula* production. During the production of the plants, day temperatures ranged from 16° C. to 18° C., night temperatures ranged from 14° C. to 16° C. and light levels averaged 4,000 lux. Plants were 13 weeks old when the photographs and description were taken. In the following description, color references are made to The Royal Horticultural Society Colour Chart, 2007 Edition, except where general terms of ordinary dictionary significance are used.

Botanical classification: *Campanula portenschlagiana* 'PTW1300101'.

Parentage:

*Female parent*.—Proprietary selection of *Campanula portenschlagiana* identified as code number PTW-1200102S, not patented.

*Male parent*.—Proprietary selection of *Campanula portenschlagiana* identified as code number PTW-1100601S, not patented.

Propagation:

*Type*.—By terminal vegetative cuttings.

*Time to initiate roots, summer*.—About ten to twelve days at temperatures about 23° to 24° C.

*Time to initiate roots, winter*.—About seven to ten days at temperatures about 22° to 23° C.

*Time to produce a rooted young plant, summer*.—About 42 days at temperatures about 23° to 24° C.

*Time to produce a rooted young plant, winter*.—About 36 days at temperatures about 22° to 23° C.

*Root description*.—Fine, fleshy; typically white in color, actual color of the roots is dependent on substrate composition, water quality, fertilizers, substrate temperature and physiological age of roots.

*Rooting habit*.—Moderately freely branching; medium density.

Plant description:

*Plant and growth habit*.—Herbaceous perennial; compact, upright to spreading and uniformly mounding plant habit; inverted triangle; moderately vigorous growth habit; numerous campanulate flowers positioned above and beyond the foliar plane.

*Plant height*.—About 12 cm.

*Plant width*.—About 24.5 cm.

*Branch description*.—Branching habit: Freely branching habit with about 70 lateral branches developing per plant. Length: About 8 cm. Diameter: About 2 mm. Internode length: About 1.4 cm. Strength: Moderately strong. Aspect: Upright to horizontal. Texture: Smooth, glabrous. Luster: Glossy. Color: Close to 144A to 144B.

Leaf description:

*Arrangement*.—Alternate, simple.

*Length*.—About 2 cm.

*Width*.—About 2.2 cm.

*Shape*.—Deltoid to broadly cordate.

*Apex*.—Bluntly acute.

*Base*.—Reniform to hastate.

*Margin*.—Coarsely dentate.

*Texture, upper surface*.—Sparsely pubescent.

*Texture, lower surface*.—Glabrous.

*Luster, upper surface*.—Slightly glossy.

*Luster, lower surface*.—Very slightly glossy.

*Venation pattern*.—Pinnate.

*Color*.—Developing leaves, upper surface: Close N137C. Developing leaves, lower surface: Close to 137C. Fully expanded leaves, upper surface: Close to N137C; venation, close to 143B. Fully expanded leaves, lower surface: Close to between 138B and 138C; venation, close to 146B.

*Petioles*.—Length: About 3.8 cm. Diameter: About 1 mm. Strength: Strong. Texture, upper and lower surfaces: Smooth. Luster, upper and lower surfaces: Glossy. Color, upper and lower surfaces: Close to 143B.

Flower description:

*Flower arrangement and flowering habit*.—Single campanulate flowers arranged in terminal and axillary simple cymes; flowers face mostly upright to outwardly; freely flowering habit with about 15 flowers developing in terminal inflorescences and about four flowers developing in axillary inflorescences; about 1,800 flowers develop per plant during the flowering season.

*Natural flowering season*.—Plants begin flowering about ten weeks after planting; relatively long flowering period, plants flower continuously from mid-May into August in The Netherlands.

*Flower longevity on the plant*.—About ten days; flowers persistent.

*Fragrance*.—Faint, sweet and somewhat musky; pleasant.

*Flower buds*.—Length: About 1.3 cm. Diameter: About 5 mm. Shape: Narrowly oblong to oblong. Color: Proximally, close to 143A; distally, close to 155B; at the base, close to 143C.

*Inflorescence height*.—About 4.2 cm.

*Inflorescence diameter*.—About 4.6 cm.

*Flower diameter*.—About 2.5 cm.

*Flower depth* (*height*).—About 1.6 cm.

*Petals*.—Quantity and arrangement: Typically five, occasionally six, in a single whorl; fused toward the lower 37.5% of the petal. Length: About 1.9 cm. Width: About 6 mm. Shape: Elliptic; recurved. Apex: Acute. Margin: Entire. Texture, upper and lower surfaces: Smooth, glabrous. Luster, upper surface: Matte. Luster, lower surface: Slightly glossy. Color: When opening, upper surface: Close to between 85C and N88D, closest to 85C; towards the base, close to NN155D. When opening, lower surface: Close to 85C; towards the apex, close to 85B; at the base, close to NN155D. Fully opened, upper surface: Close to lighter than NN155D; towards the apex, lightly tinged with close to between 85C to 85D; color does not change with development. Fully opened, lower surface: Close to lighter than NN155D; towards the apex, lightly tinged with close to 85C; color does not change with development.

*Sepals*.—Quantity and arrangement: Typically five, occasionally six, in a single whorl; fused towards the lower 33% of the sepal. Length: About 6 mm. Width: About 1.5 mm. Shape: Lanceolate. Apex: Narrowly acute. Margin: Entire. Texture, upper and lower surfaces: Glabrous. Luster, upper and lower surfaces: Matte. Color: When opening and fully opened, upper surface: Close to 143B. When opening and fully opened, lower surface: Close to 143A; towards the base, close to 143C.

*Peduncles*.—Length: About 2.6 cm. Diameter: About 1.5 mm. Aspect, flowers in terminal inflorescences: Mostly upright. Aspect, flowers in axillary inflorescences: About 35° from lateral branch axis. Strength: Moderately strong. Texture: Slightly ribbed, glabrous. Luster: Moderately glossy. Color: Close to 143C.

*Pedicels*.—Length: About 1 cm. Diameter: About 1 mm. Aspect: About 35° from peduncle axis. Strength: Moderately strong. Texture: Slightly ribbed, glabrous. Luster: Moderately glossy. Color: Close to 144C.

*Reproductive organs*.—Stamens: Quantity per flower: Typically five, occasionally six. Filament length: About 2.5 mm. Filament color: Close to NN155D. Anther shape: Lanceolate. Anther length: About 5 mm. Anther color: Close to 161D. Pollen amount: Moderate. Pollen color: Close to 4D. Pistils: Quantity per flower: One. Pistil length: About 1.3 cm. Stigma shape: Three-parted, decurrent. Stigma color: Close to NN155D. Style length: About 1.1 cm. Style color: Close to NN155D. Ovary color: Close to 143C.

*Seeds and fruits*.—Seed and fruit production has not been observed on plants of the new *Campanula*.

Disease & pest resistance: Plants of the new *Campanula* have not been noted to be resistant to pathogens and pests common to *Campanula* plants.

Garden performance: Plants of the new *Campanula* have exhibited good tolerance to rain and wind, to tolerate high temperatures about 35° C. and to be hardy to USDA Hardiness Zone 3.

It is claimed:

1. A new and distinct *Campanula* plant named 'PTW1300101' as illustrated and described.

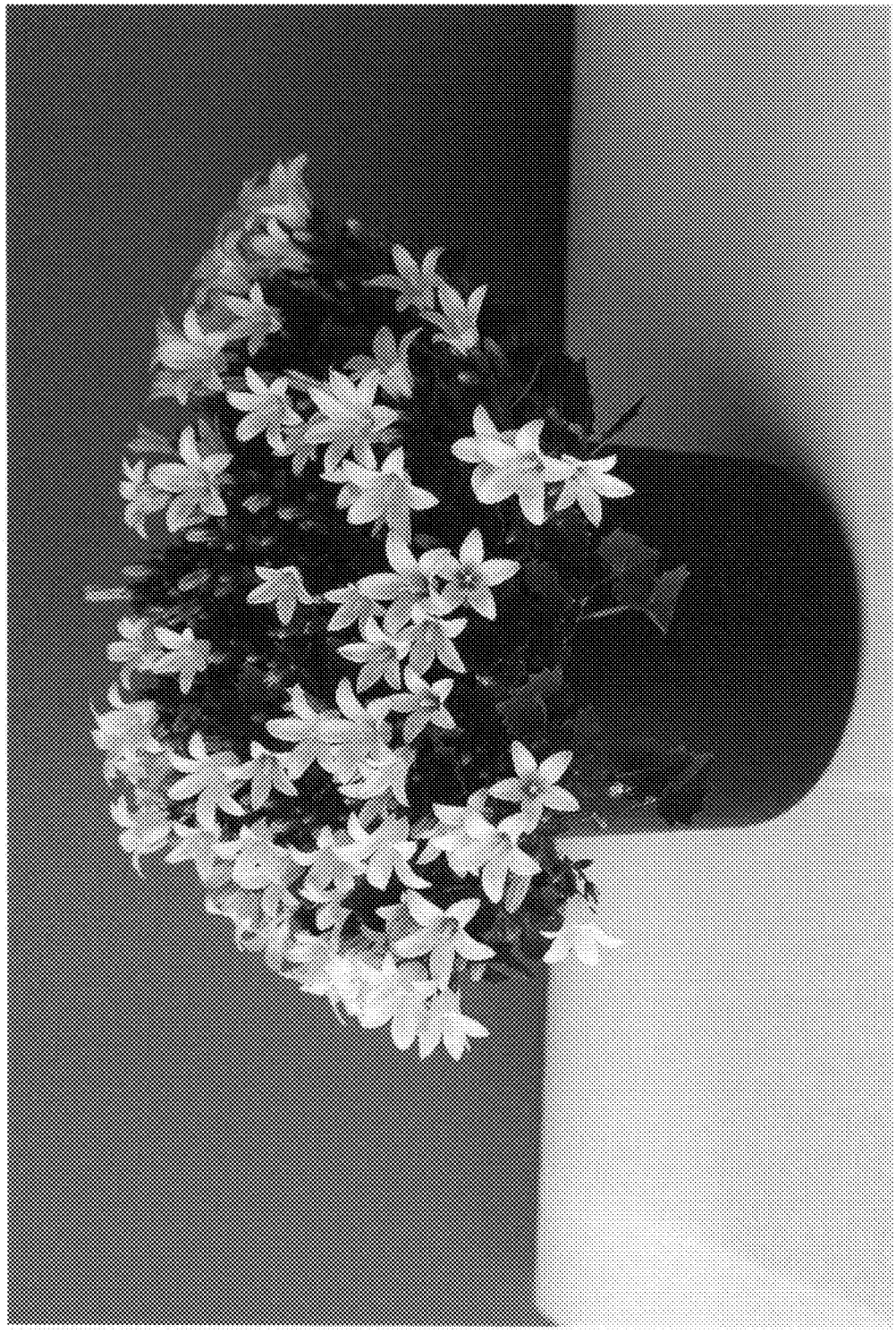

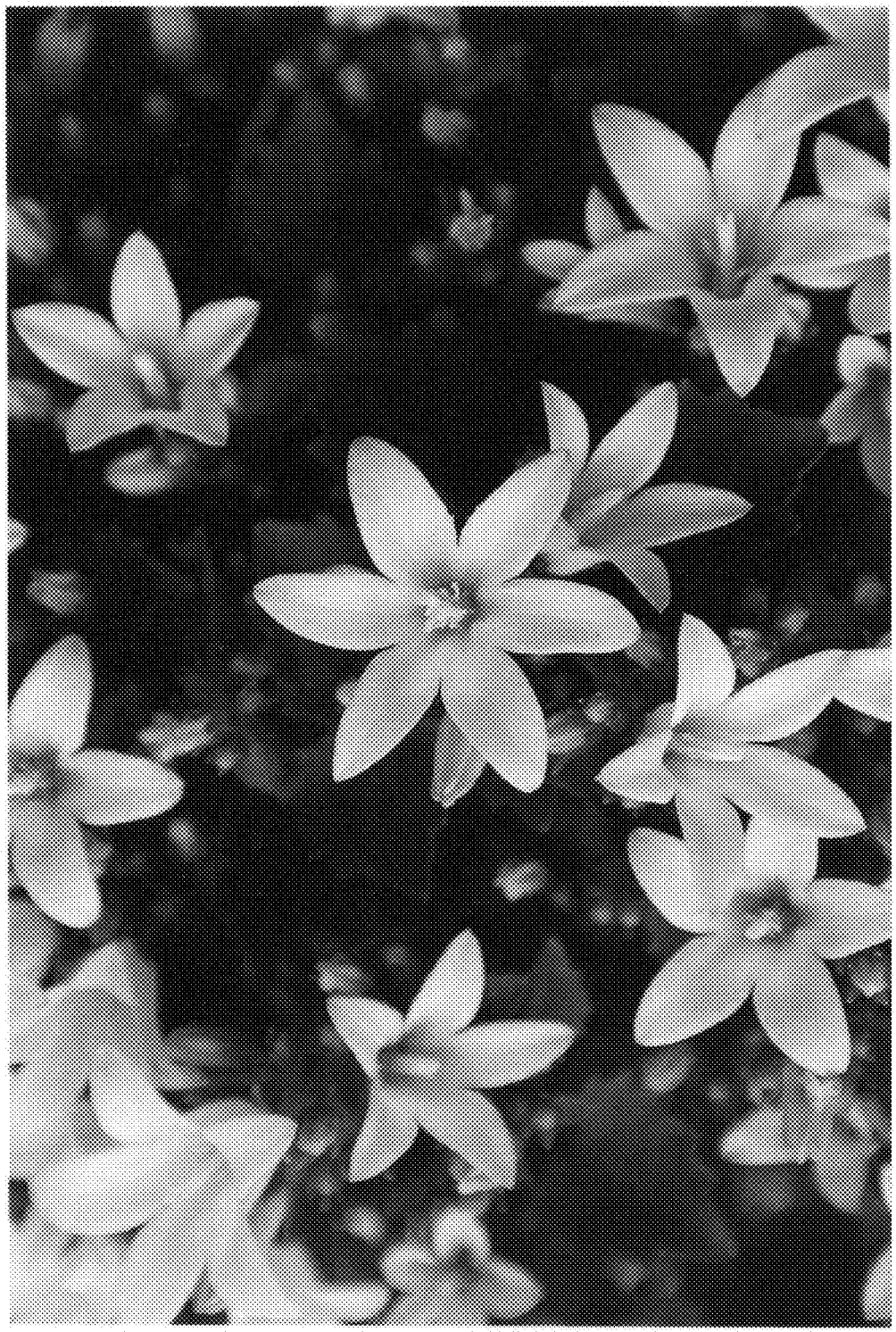

* * * * *